(12) United States Patent
Cragg et al.

(10) Patent No.: US 8,709,067 B2
(45) Date of Patent: *Apr. 29, 2014

(54) BIFURCATED ENDOLUMINAL PROSTHESIS

(75) Inventors: Andrew H. Cragg, Edina, MN (US);
Claude Mialhe, Draguignan (FR);
George Goicoechea, Freeport (BS);
John Hudson, Glenfield (GB); Michael D. Dake, Stanford, CA (US)

(73) Assignee: Lifeshield Sciences, LLC, Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/601,902

(22) Filed: Aug. 31, 2012

(65) Prior Publication Data
US 2013/0123904 A1 May 16, 2013

Related U.S. Application Data

(63) Continuation of application No. 08/312,881, filed on Sep. 27, 1994, now abandoned.

(51) Int. Cl.
*A61F 2/06* (2013.01)
(52) U.S. Cl.
USPC .......... 623/1.35; 623/1.13; 623/1.15
(58) Field of Classification Search
USPC .......... 606/108, 151–156, 194, 200; 623/1.11–1.54; 604/8
See application file for complete search history.

(56) References Cited

U.S. PATENT DOCUMENTS

| | | | | |
|---|---|---|---|---|
| 4,856,516 A | * | 8/1989 | Hillstead | 606/194 |
| 5,197,978 A | * | 3/1993 | Hess | 623/1.18 |
| 5,330,500 A | * | 7/1994 | Song | 623/1.2 |
| 5,387,235 A | * | 2/1995 | Chuter | 623/1.11 |
| 5,575,817 A | * | 11/1996 | Martin | 623/1.35 |
| 5,653,743 A | * | 8/1997 | Martin | 623/1.35 |
| 5,741,325 A | * | 4/1998 | Chaikof et al. | 623/1.35 |
| 5,800,508 A | * | 9/1998 | Goicoechea et al. | 623/1.15 |
| 7,942,919 B2 | * | 5/2011 | Goicoechea et al. | 623/1.13 |
| 8,317,854 B1 | * | 11/2012 | Ryan et al. | 623/1.35 |

* cited by examiner

*Primary Examiner* — Kathleen Holwerda
(74) *Attorney, Agent, or Firm* — Brooks, Cameron & Huebsch, PLLC (57) ABSTRACT

The present invention provides, in a first aspect a bifurcated stent for use in juxtaposition with an angelogical bifurcation. The bifurcated stent comprises a proximal portion adapted to be disposed within a blood vessel in juxtaposition with a bifurcation, a first distal stent portion adapted to extend across the bifurcation into one of the branched blood vessels, and a second distal stent portion adapted to allow blood to flow from the proximal portion into the other branch blood vessel. The invention also embraces a bifurcated prosthesis including such a bifurcated stent and a tubular graft layer formed from a biocompatible fabric in juxtaposition with the stent. In a second aspect of the invention there is provided a stent connection for joining two stents one to the other to define a continuous lumen through the two stents. Said stent connection comprises a first stent including a male engaging portion which can be compressed radially inwardly and a second stent including a female cooperating portion. Said male engaging portion can be entered into the female cooperating portion in a radially compressed state and thereafter caused or allowed to expand in the female cooperating portion to join the two stents together.

20 Claims, 4 Drawing Sheets

BIFURCATED ENDOLUMINAL PROSTHESIS

This application is a continuation of U.S. patent application Ser. No. 08/312,881, filed Sep. 27, 1994, the entire contents of which are hereby incorporated by reference.

A stent is used to provide a prosthetic intraluminal wall e.g. in the case of a stenosis to provide an unobstructed conduit for blood in the area of the stenosis. An endoluminal prosthesis comprises a stent which carries a prosthetic graft layer of fabric and is used e.g. to treat an aneurysm by removing the pressure on a weakened part of an artery so as to reduce the risk of embolism, or of the natural artery wall bursting. Typically, a stent or endoluminal prosthesis is implanted in a blood vessel at the site of a stenosis or aneurysm by so-called "minimally invasive techniques" in which the stent is compressed radially inwards and is delivered by a catheter to the site where it is required through the patient's skin or by a "cut down" technique in which the blood vessel concerned is exposed by minor surgical means. When the stent is positioned at the correct location, the catheter is withdrawn and the stent is caused or allowed to re-expand to a predetermined diameter in the vessel.

U.S. Pat. No. 4,886,062 discloses a vascular stent which comprises a length of sinuous or "zig-zag" wire formed into a helix; the helix defines a generally cylindrical wall which, in use, constitutes a prosthetic intraluminal wall. The sinuous configuration of the wire permits radial expansion and compression of the stent; U.S. Pat. No. 4,886,062 discloses that the stent can be delivered percutaneously and expanded in situ using a balloon catheter.

U.S. Pat. No. 4,733,665 discloses an expandable intraluminal graft which is constituted by a tubular member formed from a plurality of intersecting elongate members which permit radial expansion and compression of the stent.

EP-A-0556850 discloses an intraluminal stent which is constituted by a sinuous wire formed into a helix; juxtaposed apices of the wire are secured to one another so that each hoop of the helix is supported by its neighboring hoops to increase the overall strength of the stent and to minimize the risk of plaque herniation; in some embodiments the stent of EP-A-0556850 further comprises a tubular graft member to form an endoluminal prosthesis.

The prior art stents and prostheses mentioned above are generally satisfactory for the treatment of aneurysms, stenoses and other angiological diseases at sites in continuous unbifurcated portions of arteries or veins.

However, the prior art stents and prostheses are not wholly satisfactory for use where the site of desired application of the stent or prosthesis is juxtaposed or extends across a bifurcation in an artery or vein such, for example, as the bifurcation in the mammalian aortic artery into the common iliac arteries. For example, in the case of an abdominal aortic aneurysm ("AAA") in the infrarenal portion of the aorta which extends into one of the common iliac arteries, the use of one of the prior art prosthesis referred to above across the bifurcation into the one iliac artery will result in obstruction of the proximal end of the other common iliac artery; by-pass surgery is therefore required to connect the one iliac artery in juxtaposition with the distal end of the prosthesis to the other blocked iliac artery. It will be appreciated by a person skilled in the art that it is desirable to avoid surgery wherever possible; the requirement for by-pass surgery associated with the use of the prior art prosthesis in juxtaposition with a bifurcation in an artery therefore constitutes a significant disadvantage.

According to one aspect of the present invention there is provided a stent connecting means for connecting two intraluminal stents one to the other to define a continuous lumen through the two stents, said stent connecting means comprising:

a first stent including a male engaging portion which can be compressed radially inwardly; and a second stent including a female cooperating portion; wherein the male engaging portion can be entered into the female cooperating portion in a radially compressed state and thereafter caused or allowed to expand in the female cooperating portion; the arrangement being such that in service the interengagement of the male engaging portion and the female cooperating portion serves to resist longitudinal separation of the two stents one from the other.

Typically, the first stent may include a proximal male engaging portion; the second stent may include a distal female cooperation portion. The male engaging portion may be flared radially outwardly towards its extremity, and the female cooperating portion may be tapered radially inwardly towards its extremity. In some embodiments, the male engaging portion may comprise a frustoconical wall which flares outwardly towards its longitudinal extremity; the female engaging portion may comprise a frustoconical wall which tapers radially inwardly towards its longitudinal extremity.

Alternatively, said male engaging and female cooperating portions may be substantially untapered; they may be substantially cylindrical.

The male engaging portion of the first stent may be resiliently compressible in a radially inwards direction such that in the radially compressed state it is capable of self-reexpansion to engage in the female cooperating portion. Typically, each of said first and second stents may be resiliently compressible.

In use therefore the second stent may be delivered in a radially compressed state e.g. by using a catheter as described in EP-A-0556850; when the second stent is located at the site of use, the catheter may be withdrawn thereby allowing the second stent to re-expand to engage the endoluminal surface of the blood vessel.

The first stent may then be delivered percutaneously or by a "cut down" technique to a site distally of the second stent such that the male engaging portion of the first stent in the radially compressed state is entered into the expanded female cooperating portion of the second stent; the catheter may then be withdrawn allowing the first stent to re-expand such that the male engaging portion engages in the female cooperating portion of the second stent.

In some embodiments of the present invention the second stent may have two transversely spaced distal female cooperating portions; the second stent may therefore constitute a bifurcated stent for use in juxtaposition with a bifurcation in a blood vessel. Each of the two transversely spaced distal female cooperating portions may be adapted for connection to a first male stent which, in use, extends across the bifurcation into a respective one of the branched blood vessels.

In a particular aspect of the present invention there is provided a bifurcated intraluminal stent for use in juxtaposition with an angiological bifurcation; the bifurcated intraluminal stent comprising a proximal portion adapted to be positioned in service in a blood vessel in juxtaposition with a bifurcation, a first distal stent portion adapted to extend across the bifurcation in to one of the branched blood vessels and a second distal stent portion adapted to allow blood to flow from the proximal portion into the other branched vessel. The first distal stent portion may be formed integrally with the proximal portion.

In some embodiments the second distal stent portion may comprise a female cooperating portion which is adapted to engage a male engaging portion of a another stent adapted to extend in the other branched blood vessel such that, in use, the bifurcated stent can be connected in situ to the other stent. The bifurcated intraluminal stent may therefore constitute a second stent in accordance with the present invention comprising a distal female cooperating portion disposed intermediate the proximal and distal extremities of the stent; the other stent may constitute a first stent in accordance with the present invention.

Typically, the proximal end of said second stent may be flared radially outwardly towards its extremity to engage the endoluminal surface of the artery thereby to resist longitudinal movement of the second stent in service.

Each of the first and second stents may comprise a sinuous wire formed into a tubular configuration. The sinuous and tubular configurations may be imparted to the wire by winding it on a mandrel. Typically, each stent may be made from a shape memory nitinol (nickel/titanium) wire which may be wound on to the mandrel to form the stent in a tubular configuration of slightly greater diameter than the diameter of the blood vessel in which the stent is intended to be used. The stent may be annealed at an elevated temperature and then allowed to cool in air so that the nitinol wire "remembers" the configuration in which it was wound on the mandrel.

Said nitinol wire may be type "M" nitinol wire which is martensitic at temperatures below about 13° C. and is austenitic at temperatures above about 25° C.; it will be appreciated therefore that the type "M" wire will be austenitic at body temperature of 37° C. Typically, the annealing may be conducted at about 500° C. or more for at least about 60 minutes; after cooling the wire may be immersed in cold water to facilitate removal of the wire from the mandrel with the wire in its maleable martensitic form. Typically, the cold water may have temperature of less than about 10° C.; the wire may be immersed for about 5 minutes or more. An advantage of using nitinol wire to form the stent in accordance with the present invention is that the nitinol wire is "super elastic" in its austenitic state; the radial outward force exerted by the stent on the wall of the blood vessel in use is therefore substantially constant irrespective of the diameter of the vessel and the expanded stent.

In some embodiments the wire may have a helical configuration as disclosed in EP-A-0556850. Alternatively, the wire may be formed into a plurality of hoops such that the plane of the circumference of each hoop is substantially perpendicular to the longitudinal axis of the stent. Each hoop may comprise a substantially complete turn of the wire having a sinuous configuration; as each hoop is completed, the point of winding the wire may be displaced longitudinally with respect to the winding axis to form the next hoop. When the next hoop is complete, the point of winding is moved further longitudinally with respect to the winding axis to the form the next succeeding hoop and so on.

It will be appreciated that an advantage of this arrangement is that the planes of the hoops are not skewed with respect to the longitudinal axis of the stent; the longitudinal ends of the stent are "square" to said longitudinal axis, so that when the stent is caused or allowed to expand in situ there is substantially no twisting of the stent as it shortens in length. It will be appreciated that this represents a significant advantage, as in areas of stenosis or aneurysm it is desirable to minimize the movement of the stent within the blood vessel so as to reduce the potential trauma to the patient.

Typically, the stent may comprise a securing means for securing an apex of the sinuous wire in one hoop to a juxtaposed apex of a neighboring hoop so that each hoop is supported by its neighbors. The securing means may comprise a loop element to tie the juxtaposed apices together; the loop element may comprise a loop formed of a thermoplastics material such, for example, as polypropylene.

The male engaging portion and female cooperating portion of the first and second stents respectively may be formed separately from the remainder of their respective stents and then secured thereto by securing means.

The proximal and distal stent portions of the bifurcated stent in accordance with the present invention may be formed separately; the distal end of the proximal stent portion may be secured to the wider proximal end of a first intermediate frustoconical stent portion; the narrower distal end of the first intermediate frustoconical stent portion may be secured to the proximal end of the distal stent portion. The female cooperating portion of the bifurcated stent may be constituted by a second frustoconical stent portion which is secured to the distal end of the proximal stent portion in juxtaposition with the first frustoconical portion.

Alternatively the first and second frustoconical portions may be omitted; the proximal and distal stent portions may be secured directly one to the other. The female cooperating portion may be constituted by a generally cylindrical stent portion secured to said proximal stent portion in transversely spaced relation to the distal portion.

Each of the first and second stents of the present invention may carry a tubular graft layer formed from a biocompatible fabric in juxtaposition with the stent; the combined stent and graft layer constituting an endoluminal prosthesis. Typically the graft layer may be disposed externally of the stent; it will be appreciated however that in some embodiments the graft layer may be disposed internally of the stent. In some embodiments the graft layer may be secured to the stent by loop elements such, for example, as loops of polypropylene. The biocompatible fabric may be a polyester fabric or a polytetrafluoroethylene fabric; typically said fabric may be woven or a warp knitted polyester fabric. In some embodiments the woven or a warp knitted fabric may be formed in a seam-free bifurcated configuration as a sleeve for a bifurcated stent.

In some embodiments the male engaging portion of the first stent and the female cooperating portion of the second stent may be left uncovered. Alternatively, the fabric graft layer may extend to the proximal extremity on the external surface of the male engaging portion, and may be folded over the distal extremity of the female engaging portion to form an inner sleeve; in use the external fabric of the male engaging portion may butt against the folded over portion of the fabric internally of the female cooperating portion to form a substantially blood-tight seal.

The present invention in one aspect therefore includes a bifurcated endoluminal prosthesis comprising a bifurcated stent in accordance with the invention and a tubular graft layer.

The bifurcated prosthesis may be adapted for use in the infrarenal portion of a mammalian aorta in juxtaposition with the bifurcation of the common iliac arteries for the treatment of abdominal aortic aneurysms. In use the bifurcated endoluminal prosthesis may be introduced into the infrarenal portion of the aorta e.g. using a catheter as described in EP-A-0556850 such that the first distal stent portion extends into one of the branched iliac arteries; the catheter may then be withdrawn allowing the prosthesis to re-expand in situ.

The other stent may also have a tubular graft layer. If required the other prosthesis may be introduced in a radially compressed state such that the male engaging portion of the other prosthesis is engaged in the intermediate female cooperating portion of the bifurcated prosthesis; the other prosthesis is then caused to be allowed to re-expand in situ such that the male engaging portion engages in the female cooperating portion to resist longitudinal separation of the two prosthesis in service.

It will be appreciated by a person skilled in the art that the prostheses may be introduced to the site of use percutaneously or by "cut down" techniques.

The present invention in one aspect therefore includes a bifurcated endoluminal prosthesis comprising a bifurcated stent in accordance with the invention and a tubular graft layer; the bifurcated prosthesis may be adapted for use in the infrarenal portion of a mammalian aorta in juxtaposition with the bifurcation of the common iliac arteries for the treatment of abdominal aortic aneurysms. In use therefore the bifurcated endoluminal prosthesis may be introduced into the infrarenal portion of the aorta e.g. using a catheter as described in EP-0556850 such that the first distal stent portion extends into one of the branched iliac arteries; the catheter may then be withdrawn allowing the prosthesis to re-expand in situ. The other stent may also have a tubular graft layer. If required the other prosthesis may be introduced in a radially compressed state such that the male engaging portion of the other prosthesis is engaged in the intermediate female cooperating portion of the bifurcated prosthesis; the other prosthesis is then caused to be allowed to re-expand in situ such that the male engaging portion engages in the female cooperating portion to resist longitudinal separation of the two prosthesis in service. It will be appreciated by a person skilled in the art that the prosthesis may be introduced to the site of use percutaneously or by "cut down" techniques.

The second stent may be provided on its external surface with circumferentially spaced wire barbs or hooks adapted to engage in the endoluminal surface of the host artery to resist longitudinal movement or slippage of the stent in use. Typically the barbs or hooks may be disposed on part of the stent which is provided with a fabric graft layer such that in use the points of the artery which are engaged by the barbs or hooks are covered by the fabric graft. It will be appreciated by a person skilled in the art that the trauma to the artery wall caused by the hooks or barbs may cause emboli; the provision of the fabric graft over the barbs or hooks in use will therefore help to prevent the introduction of such emboli into the blood stream.

The male engaging portion for the first stent may be provided with circumferentially spaced hooks or barbs on its external surface to engage the internal surface of said female cooperating means, thereby to reinforce the connecting means against longitudinal separation of the stents one from the other in the service.

The present invention therefore provides a connecting means for connecting two stents longitudinally one to the other. It will be appreciated that this represents a significant step forward in the art as it allows the provision of a bifurcated endoluminal prosthesis for use in juxtaposition e.g. with arterial bifurcations without requiring by-pass surgery to connect one of the branched arteries to the other branched artery.

In particular, the invention provides a bifurcated endoluminal prosthesis which can be positioned in an artery in juxtaposition with a bifurcation to extend into one of the branched arteries; the bifurcated prosthesis can be connected to another prosthesis which extends into the other branched artery. The prosthesis can be delivered percutaneously or by "cut down" methods and connected together in situ thereby to provide effective treatment of an angiological disease such, for example, as an aneurysm or a stenosis which extends across a bifurcation in a blood vessel without the need for by-pass surgery.

Following is a description by way of example only and with reference to the accompanying drawings of methods of carrying the present invention into effect.

In the drawings:

FIG. 1b is a front view of another stent which is adapted to be connected to the bifurcated stent of FIG. 1a;

Figure 1A:
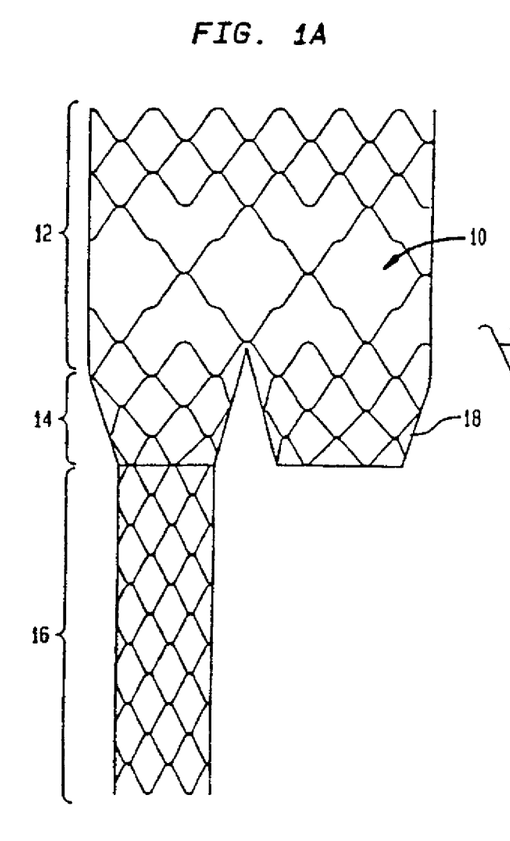
FIG. 1a is a front view of a bifurcated intraluminal stent in accordance with the present invention constituting part of an endoluminal prosthesis.

A bifurcated stent in accordance with the present invention which is indicated at (10) in FIG. 1a comprises a wire skeleton which is constructed in four separate parts, namely a proximal part (12) a first frustoconical part (14) a second distal part (16) and a second frustoconical part (18). Said bifurcated stent (10) carries a fabric graft layer (not shown) for use as an endoluminal prosthesis e.g. in the infrarenal portion of a mammalian aorta in juxtaposition with the bifurcation of the common iliac arteries. It will be appreciated, however, that bifurcated stents (with or without fabric graft layers) for use in different parts of the angiological system and for different mammals can be constructed in accordance with the invention by varying the dimensions of the stent accordingly.

Each of the four parts of the bifurcated stent (10) is made in substantially the same way by winding a shape memory nitinol wire, typically nitinol type M wire, onto a mandrel.

Figure 2:
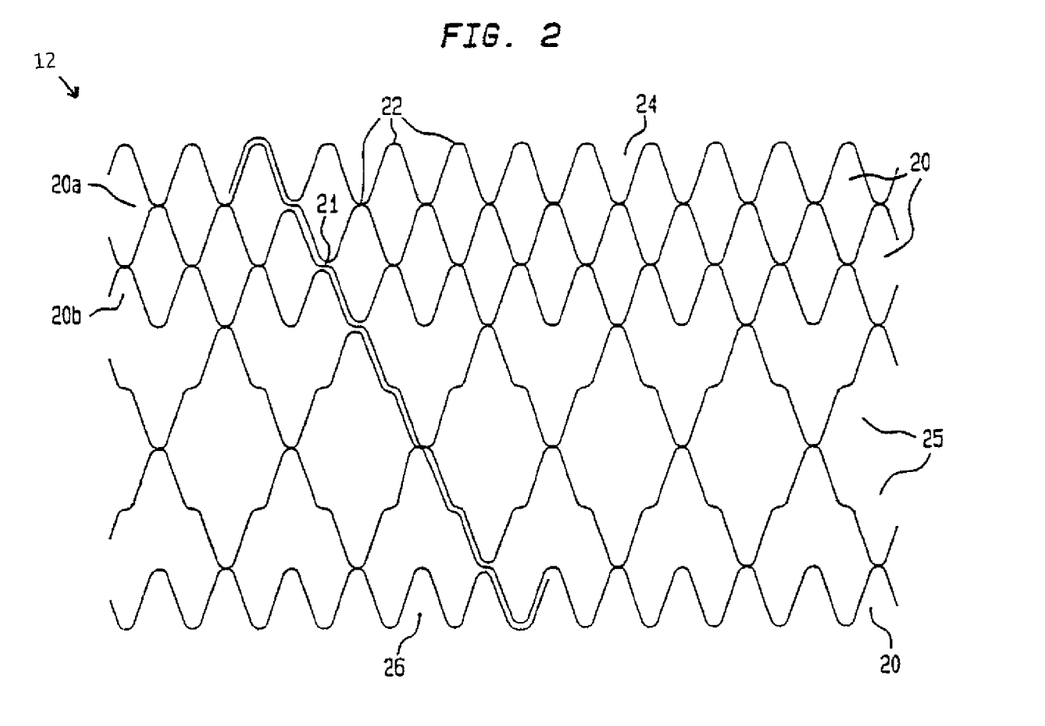
FIG. 2 is a side view of part of the bifurcated stent of FIG. 1a opened up to show its construction.

The construction of the proximal part (12) of the bifurcated stent (10) is shown in FIG. 2; nitinol wire type M wire having a diameter of 0.46 mm (0.018") is wound around the mandrel to form a plurality of hoops (20). The winding surface of the mandrel is provided with a plurality of upstanding pins disposed in a zig-zag pattern for each of the hoops (20) so that in each hoop (20) the nitinol wire follows a sinuous path to define a plurality of circumferentially spaced apices (22). Each hoop is wound onto the mandrel such that the plane of the circumference of each hoop is substantially perpendicular to the longitudinal axis of the mandrel. When one hoop (20) e.g. the hoop indicated at ($20^a$) has been formed, the point of winding of the nitinol wire is displaced longitudinally with respect to the mandrel axis to form the next successive hoop ($20^b$) as shown at (21) in FIG. 2.

The proximal part of the bifurcated stent is formed on the mandrel with a diameter of about 24 mm and a length in the longitudinal direction of about 55 mm. From FIGS. 1a and 2 it will be noted that the proximal part (12) is constituted by three hoops (20) of unit width at the proximal end (24) of the proximal part (12), two intermediate hoops (25) of twice unit width and, at its distal end (26), by a single hoop (20) of unit width. When the nitinol wire has been wound onto the mandrel, the nitinol wire is annealed at an elevated temperature and then allowed to cool.

In this embodiment of the invention the wire is annealed at a temperature of about 500° C. for 60 minutes and is then allowed to cool in air. The purpose of the annealing is so that the nitinol wire in its austenitic form "remembers" its configuration as wound on the mandrel; it will be appreciated therefore that other temperatures and durations for the annealing are included within the present invention provided the nitinol wire "remembers" its wound configuration.

After annealing and cooling, the wire is immersed in cold water at less than 10° C. for about 5 minutes; the wire is then removed from the mandrel, and juxtaposed apices (22) of neighboring hoops (20) are secured together using, in this example, 0.003" polypropylene filaments. In the proximal part shown in FIG. 2, each apex (22) of each hoop (20) which has a juxtaposed apex of a neighboring (20) is tied to the juxtaposed apex (22). It will be appreciated, however, that in other embodiments of the invention only some of the juxtaposed apices (22) may be secured in this way.

Figure 3:
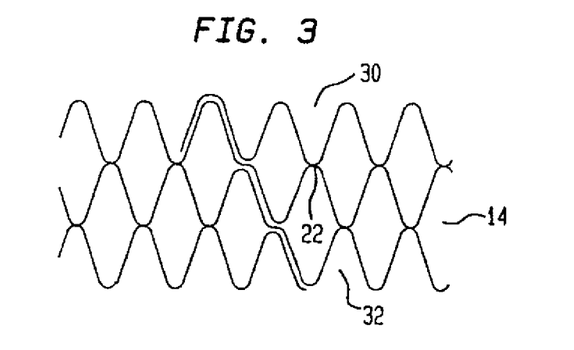
FIG. 3 is a side view of another part of the bifurcated stent of FIG. 1a opened up to show its construction.

The first and second frustoconical parts (14, 18) of the skeleton are formed in substantially the same way as the proximal part (12) by winding nitinol wire onto a mandrel and then annealing the wire before removing it from the mandrel. As shown in FIG. 3, the first and second frustoconical parts (14, 18) are each constituted by three hoops (20) of unit width. The mandrel is tapered such that the proximal end of each of the frustoconical parts (14, 18) is fowled with a diameter of about 12 mm and the distal end (32) of each is formed with a diameter of about 9 mm. The overall length of each of the frustoconical parts (14, 18) is about 18 mm. The wire used for the frustoconical parts (14, 18) is nitinol type M wire having a diameter of 0.28 mm (0.011"). Juxtaposed apices (22) of each of the frustoconical parts (14, 18) are tied together using 0.03" polypropylene filaments as described above. The first and second frustoconical parts (14, 18) are secured to the distal end (26) of the proximal part (12) of the stent (10) in transversely spaced relation as shown in FIG. 1a by securing the apices (22) of the hoop (20) forming the wider proximal end (30) of each of the frustoconical parts (14, 18) to juxtaposed apices (22) of the hoop (20) on the distal end (26) of the proximal part (12).

Figure 4:
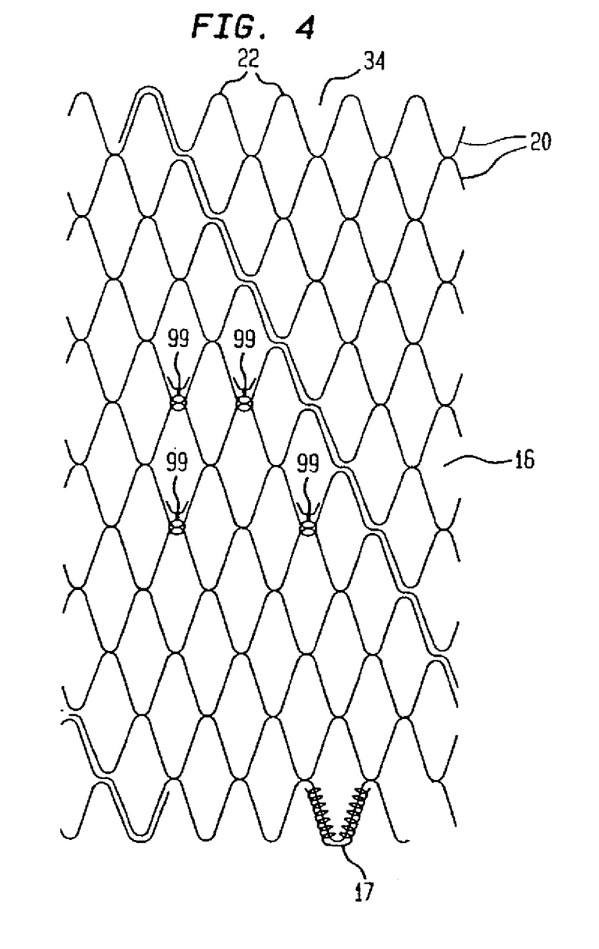
FIG. 4 is a side view of yet another part of the bifurcated stent of FIG. 1a opened up to show its construction.

The distal part (16) of the bifurcated stent (10) is formed by winding nitinol type M wire having a diameter of 0.28 mm (0.011") onto a mandrel to form twelve longitudinally spaced hoops (20) as shown in FIG. 4; the distal part has an overall length of about 66 mm and a uniform diameter of about 9 mm. The proximal end (34) of the distal part (16) is secured to the narrower distal end (32) of the first frustoconical part (14) by tying each apex (22) on the proximal end (34) of the distal part (16) to a juxtaposed apex on the distal end (32) of the first frustoconical part (14) using 0.003" polypropylene filaments.

The proximal part (12), the first and second frustoconical parts (14, 18), and the distal part (16) are each covered with a tubular graft layer of a biocompatible woven fabric (not shown) such, for example, a plain woven fabric made from 30 or 40 deniers polyester. The tubular fabric layers are attached to the proximal and distal parts (12, 16) of the stent (10) by stitching with 0.003" polypropylene filaments around the apices (22) of the underlying skeleton. The fabric covered stent constitutes an endoluminal prosthesis.

The proximal part (12) of the wire skeleton is provided with a plurality of circumferentially spaced hooks or barbs (not shown) which project through the tubular fabric layer to engage in the endoluminal surface of a host artery in service.

The sinuous configuration of each turn (20) of the wire skeleton of the stent (10) allows the prosthesis to be compressed resiliently radially inwards so that it can be received in a catheter e.g. a 16 or 18 French catheter for percutaneous or "cut down" delivery e.g. to an intraluminal site in the infrarenal section of the aortic artery. Larger diameter catheters up to, say, 20 French may be used to deliver the prosthesis using "cut down" procedures.

X-ray opaque markers (not shown) are attached to the stent so that the delivery of the stent can be monitored using x-rays. As radio-opaque markers may be used a gold or platinum wire crimped onto the proximal end of the stent; typically the markers may be secured to the stent in line with the distal stent portion so that the distal stent portion can be aligned with and inserted into one of the branched arteries in situ. The bifurcated endoprosthesis is positioned in the infrarenal section of the aortic artery in juxtaposition with the bifurcation of the common iliac arteries such that the distal part (16) of the prosthesis extends into one of the common iliac arteries. The catheter is then withdrawn allowing the stent (10) to re-expand towards its configuration as wound on the mandrel in which it was annealed until the stent engages the endoluminal surface of the host artery.

The barbs or hooks engage the endoluminal surface of the host artery to resist longitudinal displacement or slipping of the prosthesis in use.

It will be appreciated that when the bifurcated prosthesis is positioned and re-expanded in the fitted position, blood can flow from the aortic artery into the proximal part (12) of the prosthesis from where it can flow into the one common iliac artery through the frustoconical part (14) and the distal part (16) and also into the other common iliac artery through the second frustoconical part (18).

Figure 1B:
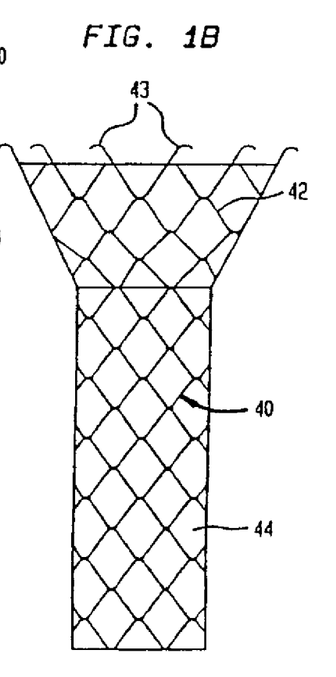

In cases where it is required to implant a prosthesis in the other common iliac artery a second prosthesis comprising a second stent (40) as shown in FIG. 1b can be used. The second stent (40) includes a wire skeleton comprising a proximal frustoconical part (42) and a distal part (44). The distal part (44) of the second stent (40) is covered with a tubular graft layer of a biocompatible fabric such, for example, as polyester or polytetrafluoroethylene fabric (not shown).

The frustoconical proximal part (42) is constructed in the same way as the frustoconical parts (14, 18) of the bifurcated stent (10); the distal part (44) is constructed in the same way as the distal part (16) of the bifurcated stent (10). The distal end of the frustoconical proximal part (42) is secured to the proximal end of the distal part (44) by securing juxtaposed apices using polypropylene filaments as described above.

In use, the second prosthesis is compressed radially inwards and is received in a catheter for percutaneous or "cut down" delivery to the other common iliac artery. The frustoconical proximal part (42) is guided, in the radially compressed state, into the second frustoconical part (18) of the bifurcated stent (10). The catheter is then withdrawn allowing the second stent (40) to re-expand towards its remembered configuration, until the distal part (14) engages the endoluminal surface of the other common iliac artery, and the outer surface of the frustoconical proximal part (42) engages the interior surface of the second frustoconical part (18) of the bifurcated stent (10).

The frustoconical proximal part (42) may be formed with circumferentially spaced barbs or hooks (not shown) which engage in the wire skeleton of the second frustoconical part (18) of the bifurcated stent (10). The tapered configurations of the second frustoconical part (18) of the bifurcated stent (10) and of the proximal frustoconical part (42) of the second stent (40) are such that in the fitted position as described, the prostheses are locked together to resist longitudinal separation in service, the barbs or hooks on the second stent (40) help to resist such longitudinal separation.

Figure 5:
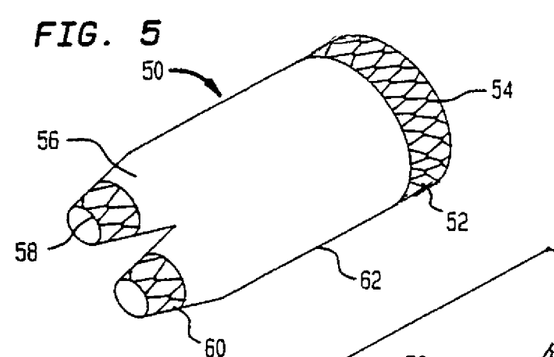
FIG. 5 is a schematic perspective view of a bifurcated endoluminal prosthesis in accordance with the present invention.

In another example of the present invention a bifurcated endoluminal prosthesis (50) as shown in FIG. 5 includes a bifurcated stent comprising a proximal portion (52) which tapers radially inwardly from its proximal end (54) to its distal end (56), and first and second transversely spaced frustoconical distal portions (58, 60) which are secured to the distal end (56) of the proximal portion (52); the proximal portion (52) is covered with a tubular graft layer of a biocompatible fabric (62).

In use the prosthesis is delivered percutaneously or by "cut down" methods to an artery in juxtaposition with an arterial bifurcation; blood can flow through the frustoconical proximal portion (52) into each of the branched arteries through the first and second distal frustoconical portions (58, 60). If a prosthesis is required in one or both of the branched arteries, a separate prosthesis comprising a stent of the type shown in FIG. 1b referred to above covered with fabric can be connected to the bifurcated prosthesis (50) by inserting and re-expanding the proximal end of such a separate prosthesis in one or both of the distal frustoconical portions (58, 60) of the prosthesis (50) for engagement therein.

Figures 6, 7:
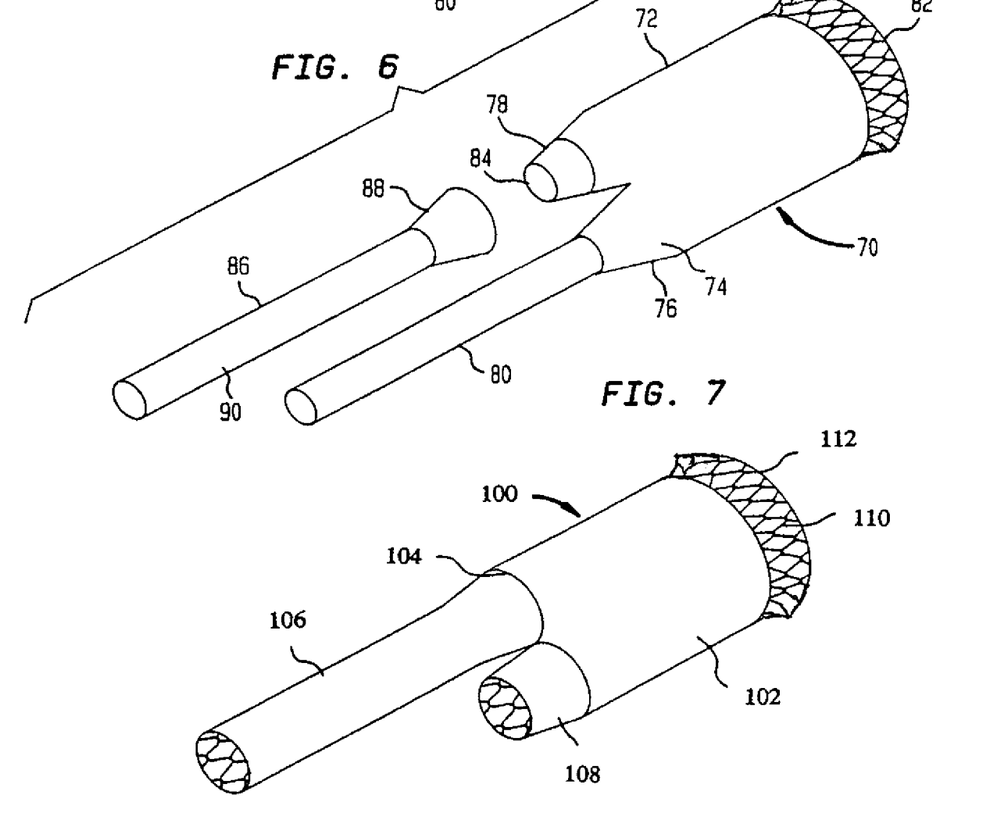
FIG. 6 is a schematic view of another bifurcated endoluminal prosthesis in accordance with the present invention.
FIG. 7 is a schematic view of yet another bifurcated endoluminal prosthesis in accordance with the present invention.

Another variant of the present invention is shown in FIG. 6 which shows a bifurcated endoluminal prosthesis (70) having a proximal portion (72) which is secured at its distal end (74) to two transversely spaced frustoconical intermediate portions (76, 78). One of said frustoconical intermediate portions (76) is secured at its distal end to an elongate distal portion (80). The proximal end (82) of the proximal portion (72) is flared radially outwards towards its proximal end (82) to engage the intraluminal surface of the host blood vessel in service. Save for this flared portion, the entire endoprosthesis is covered with a fabric graft layer as shown in FIG. 6; said graft layer is carried externally of the wire skeleton and is folded over the distal extremity (84) of the other frustoconical intermediate portion (78) to form an internal lining in said other frustoconical immediate portion (78).

Said other frustoconical intermediate portion (78) constitutes a female cooperating portion in accordance with the present invention which is adapted to receive a male engaging portion of another prosthesis as indicated at (86) in FIG. 6. Said other prosthesis (86) includes a frustoconical proximal portion (88) which constitutes the male engaging portion and an elongate distal portion (90). The whole of the other prosthesis (86) is covered with a fabric graft layer as shown in FIG. 6. In service, the male engaging portion (88) of the other prosthesis (86) is entered into and engaged with the female cooperating portion (78) of the bifurcated prosthesis (70) in situ in the manner hereinbefore described. The fabric layer on the male engaging portion (88) butts face-to-face on the folded over portion of the fabric layer disposed internally of the female cooperating portion (78) to form a substantially blood-tight seal therewith.

Yet another example of the present invention is shown in FIG. 7 in which a bifurcated endoluminal prosthesis (100) has a generally cylindrical proximal portion (102); said proximal portion (102) is connected at its distal end (104) to an elongate, generally cylindrical distal portion (106). Said proximal portion (102) is also connected at its distal end (104) to a generally cylindrical intermediate portion (108) which is secured in transversely spaced relation to the elongate distal portion (106). Said cylindrical intermediate portion (108) constitutes a female engaging portion which is adapted to receive a generally cylindrical male engaging portion of a second elongate prosthesis (not shown). The male engaging portion is equipped with circumferentially spaced external barbs to engage in the female cooperating portion in service. As shown in FIG. 7, the whole of the bifurcated prosthesis (100) is covered with an external fabric graft layer save for a flared portion (110) towards the proximal end (112) of the proximal portion (102).

The invention claimed is:

1. A bifurcated stent having an assembly bifurcation for use with an angiological bifurcation of a blood vessel into two branched vessels comprising:
    a proximal stent portion adapted to be disposed within said blood vessel,
    a first stent comprising the proximal stent portion, an intermediate stent portion, and a first distal stent portion adapted to extend across the angiological bifurcation into one of the branched vessels,
    the intermediate stent portion extending distally relative to said assembly bifurcation, and
    a second stent comprising a second distal stent portion joined to said intermediate stent portion of said first stent and adapted to allow blood to flow from said proximal stent portion into the other branched vessel,
    wherein said proximal stent portion, said first distal stent portion, and said second distal stent portion each comprises a wire following a sinuous path to define a plurality of circumferentially spaced apices formed into a tubular configuration,
    wherein said wire defines a plurality of hoops such that a plane of a circumference of each hoop is disposed substantially perpendicular to a longitudinal axis of said bifurcated stent,
    wherein each hoop comprises a substantially complete turn of the wire having a sinuous configuration,
    wherein, at an end of each hoop, said wire is displaced longitudinally with respect to a winding axis of said wire to form a next hoop,
    wherein said plane of the circumference of each hoop is not skewed with respect to said longitudinal axis of said bifurcated stent,
    wherein each longitudinal end of said bifurcated stent is square to said longitudinal axis of said bifurcated stent,
    wherein said intermediate stent portion comprises a frustoconical female cooperating portion that is tapered radially inward from its proximal end to its distal end,
    wherein said second stent has a frustoconical male engaging portion that is tapered radially inward from its proximal end to its distal end adapted to engage said frustoconical female cooperating portion, such that said intermediate stent portion is configured to be joined in situ to said second stent,
    wherein said frustoconical male engaging portion terminates at a proximal end of said second stent and said frustoconical female cooperating portion terminates at a distal end of said intermediate stent portion and wherein a distal orifice at said distal end of said intermediate stent portion remains in an expanded configuration after being joined to said male engaging portion, and
    wherein a proximal end of said proximal stent portion is flared radially outwardly towards its extremity and adapted to engage an endoluminal surface of said blood vessel, thereby to resist longitudinal movement of said bifurcated stent in service, and wherein said proximal stent portion, other than said proximal end of said proximal stent portion, is generally cylindrical.

2. The bifurcated stent as claimed in claim 1 wherein said first distal stent portion is formed integrally with said proximal stent portion.

3. The bifurcated stent as claimed in claim 1 wherein said bifurcated stent is made from a shape memory nitinol wire having a tubular configuration and a diameter greater than a diameter of the blood vessel in which said bifurcated stent is intended to be used.

4. The bifurcated stent as claimed in claim 1 further comprising securing means for securing an apex of the sinuous wire in one hoop to a juxtaposed apex of a neighboring hoop so that each hoop is supported by its neighbors.

5. The bifurcated stent as claimed in claim 4 wherein said securing means comprises a loop element to tie the juxtaposed apices together.

6. The bifurcated stent as claimed in claim 1 wherein:
a graft layer formed from a bio-compatible fabric is disposed in juxtaposition with said bifurcated stent, and
barbs are disposed on said bifurcated stent and at least partially covered by said fabric to secure a prosthesis comprising said bifurcated stent to said blood vessel.

7. The bifurcated stent as claimed in claim 6 wherein said barbs are attached to said bifurcated stent and project through said fabric.

8. The bifurcated stent as claimed in claim 1, further comprising two graft layers disposed in juxtaposition with a prosthesis comprising said bifurcated stent.

9. The bifurcated stent as claimed in claim 8 wherein:
said two graft layers include a first graft layer and a second graft layer;
said first graft layer is disposed internally of said intermediate stent portion; and
said second graft layer is disposed externally of said second stent.

10. The bifurcated stent as claimed in claim 8 wherein:
said two graft layers include a first graft layer and a second graft layer;
said first graft layer is disposed externally of said frustoconical female cooperating portion and folds over a distal extremity of said frustoconical female cooperating portion to form an inner sleeve; and
said second graft layer is disposed externally of said frustoconical male engaging portion and contacts said inner sleeve to form a blood-tight seal.

11. The bifurcated stent as claimed in claim 1 wherein at least one of said first and second stents includes a portion having a graft layer disposed internally and externally of said at least one of said first and second stents.

12. A bifurcated stent having an assembly bifurcation for use with an angiological bifurcation of a blood vessel into two branched vessels comprising:
a proximal stent portion adapted to be disposed within said blood vessel,
a first stent comprising the proximal stent portion, an intermediate stent portion, and a first distal stent portion adapted to extend across the angiological bifurcation into one of the branched vessels,
the intermediate stent portion extending distally relative to said assembly bifurcation, and
a second stent comprising a second distal stent portion joined to said intermediate stent portion of said first stent and adapted to allow blood to flow from said proximal stent portion into the other branched vessel,
wherein said proximal stent portion, said first distal stent portion, and said second distal stent portion each comprises a wire following a sinuous path to define a plurality of circumferentially spaced apices formed into a tubular configuration,
wherein said wire defines a sinuous configuration of a plurality of hoops comprising a substantially complete turn of the wire such that a plane of a circumference of each hoop is disposed substantially perpendicular and is not skewed with respect to a longitudinal axis of said bifurcated stent,
wherein, at an end of each hoop, said wire is displaced longitudinally with respect to a winding axis of said wire to form a next hoop,
wherein each longitudinal end of said bifurcated stent is square to said longitudinal axis of said bifurcated stent,
wherein a frustoconical male engaging portion tapered radially inward from its proximal to its distal end terminates at a proximal end of said second stent and a frustoconical female cooperating portion tapered radially inward from its proximal end to its distal end terminates at a distal end of said intermediate stent portion and wherein a distal orifice at said distal end of said intermediate stent portion remains in an expanded configuration after being joined to said male engaging portion, and
wherein a proximal end of said proximal stent portion is flared radially outwardly towards its extremity and adapted to engage an endoluminal surface of said blood vessel, thereby to resist longitudinal movement of said bifurcated stent in service, and wherein said proximal stent portion, other than said proximal end of said proximal stent, is generally cylindrical.

13. The bifurcated stent as claimed in claim 12 wherein said first distal stent portion is formed integrally with said proximal stent portion.

14. The bifurcated stent as claimed in claim 12 further comprising securing means for securing an apex of the sinuous wire in one hoop to a juxtaposed apex of a neighboring hoop so that each hoop is supported by its neighbors.

15. The bifurcated stent as claimed in claim 14 wherein said securing means comprises a loop element to tie the juxtaposed apices together.

16. A bifurcated stent having an assembly bifurcation for use with an angiological bifurcation of a blood vessel into two branched vessels comprising:
a first stent comprising a first distal stent portion adapted to extend across the angiological bifurcation into one of the branched vessels, and an intermediate stent portion extending distally relative to said assembly bifurcation, and
a second stent comprising a second distal stent portion joined to said intermediate stent portion of said first stent and adapted to allow blood to flow from said proximal stent portion into the other branched vessel,
wherein a wire defines a sinuous configuration of a plurality of hoops comprising a substantially complete turn of said wire such that a plane of a circumference of each hoop is disposed substantially perpendicular and is not skewed with respect to a longitudinal axis of said bifurcated stent,
wherein, at an end of each hoop, said wire is displaced longitudinally with respect to a winding axis of said wire to form a next hoop,
wherein each longitudinal end of said bifurcated stent is square to said longitudinal axis of said bifurcated stent, and
wherein a frustoconical male engaging portion tapered radially inward from its proximal to its distal end terminates at a proximal end of said second stent and a frustoconical female cooperating portion tapered radially inward from its proximal end to its distal end terminates at a distal end of said intermediate stent portion and wherein a distal orifice at said distal end of said intermediate stent portion remains in an expanded configuration after being joined to said male engaging portion.

17. The bifurcated stent as claimed in claim 16, further comprising two graft layers disposed in juxtaposition with a prosthesis comprising said bifurcated stent.

18. The bifurcated stent as claimed in claim 17 wherein:
said two graft layers include a first graft layer and a second graft layer;
said first graft layer is disposed internally of said intermediate stent portion; and
said second graft layer is disposed externally of said second stent.

19. The bifurcated stent as claimed in claim 17 wherein:
said two graft layers include a first graft layer and a second graft layer;
said first graft layer is disposed externally of said frustoconical female cooperating portion and folds over a distal extremity of said frustoconical female cooperating portion to form an inner sleeve; and
said second graft layer is disposed externally of said frustoconical male engaging portion and contacts said inner sleeve to form a blood-tight seal.

20. The bifurcated stent as claimed in claim 16 wherein at least one of said first and second stents includes a portion having a graft layer disposed internally and externally of said at least one of said first and second stents.

* * * * *